(12) United States Patent
Zheng et al.

(10) Patent No.: US 6,187,992 B1
(45) Date of Patent: Feb. 13, 2001

(54) TRANSGENIC MOUSE HAVING A DISRUPTED AMYLOID PRECURSOR PROTEIN GENE

(75) Inventors: Hui Zheng; Howard Y. Chen; Myrna E. Trumbauer; Leonardus H. T. van der Ploeg, all of Rahway, NJ (US); Guy Seabrook; Dalip Sirinathsinghji, both of Harlow (GB)

(73) Assignees: Merck & co., Inc., Rahway, NJ (US); Merck Frosst Canada & Co., Kirkland (CA)

( * ) Notice: Under 35 U.S.C. 154(b), the term of this patent shall be extended for 0 days.

(21) Appl. No.: 09/266,475

(22) Filed: Mar. 11, 1999

Related U.S. Application Data

(63) Continuation-in-part of application No. 08/849,487, filed on Jun. 5, 1997, now abandoned, and a continuation of application No. PCT/US95/15672, filed on Dec. 1, 1995, and a continuation-in-part of application No. 08/349,334, filed on Dec. 5, 1994, now abandoned.

(51) Int. Cl.$^7$ ....................... A01K 67/00; A01K 67/027; G01N 33/00; C12N 15/00; C12N 5/08
(52) U.S. Cl. ................... 800/12; 800/3; 800/18; 800/25; 435/354
(58) Field of Search .................. 800/3, 12, 18, 800/25; 435/354

(56) References Cited

FOREIGN PATENT DOCUMENTS

| | | |
|---|---|---|
| PCT WO92/13069 | 8/1992 | (WO) . |
| PCT WO93/14200 | 7/1993 | (WO) . |

OTHER PUBLICATIONS

Bradley, et al., "Modifying The Mouse: Design and Desire", Biotechnology, vol. 10, pp. 534–539, 1992.

Capecchi, et al., "Altering the Genome by Homologous Recombination", Science, vol. 244, pp. 1288–1292, Jun. 16, 1989.

Capecchi, et al., "The New Mouse Genetics: Altering the Genome by Gene Targeting", Trends in Genetics, vol. 5, pp. 70–76, 1989.

Jaenisch, "Transgenic Animals", Science, vol. 240, pp. 1468–1474, 1988.

Tocci, et al., "Expression in *Escherichia Coli* of Fully Active Recombinant Human IL 1β: Comparison with Native Human IL 1β", Journal of Immunol., vol. 138, pp. 1109–1114, 1987.

Chen, et al., "A Lymphoproliferative Abnormality Associated with Inappropriate Expression of the Thy–1 Antigen in Transgenic Mice", Cell, vol. 51, pp. 7–19, Oct. 9, 1987.

Mansour, et al., "Disruption of the proto–oncogene int–2 in mouse embryo–derived stem cells: a general strategy for targeting mutations in non–selectable genes", Nature, vol. 336, pp. 348–352, 1988.

Yamada, et al., "Complementary DNA For The Mouse Homolog Of The Human Amyloid Beta Protein Precursor", Biochemical and Biophysical Research Communication, vol. 149, No. 2, 1987, pp. 665–671.

Defeudis, "Beta–Amyloid Protein in Transgenic Mice", Drug News Perspective, vol. 10, pp. 617–619, 1991.

Selkoe, "Alzheimer's Disease: In the Beginning", Nature, vol. 354, Dec. 12, 1991, pp. 432–433.

Fassler, et al., "Knockout Mice: How to Make Them and Why. The Immunological Approach", Int. Arch. Allergy Immunol., vol. 106, pp. 323–334, 1995.

Izumi, et al., "Positive and negative regulatory elements for the expression of the Alzheimer's disease amyloid precursor–encoding gene in mouse", Gene, vol. 112, pp. 189–195, 1992.

Sambrook, et al., "Cosmid Vectors", Cold Spring Harbor Lab. Press, pp. 3.1–3.3, 1989.

Robertson, et al., "Germ–line transmission of genes introduced into cultured pluripotential cells by retroviral vector", Letters to Nature, vol. 323, pp. 445–448, 1986.

Bradley, et al., "Production and Analysis of Chimeric Mice", In Teratocarcinomas and Embryonic Stem Cells: A Practical Approach, pp. 113–151, 1987.

Seabrook, et al., "Modulation of Long–Term Potentiation in CA1 Region of Mouse Hippocampal Brain Slices by GABAA Receptor Benzodiazepine Site Ligands", Neuropharmacology, vol. 36, No. 6, pp. 823–830, 1997.

Kim, et al., "Recombinant fragment assay for gene targeting based on the polymerase chain reaction", Nucleic Acids Research, vol. 16, No. 18, 1988, pp. 8887–8903.

Evans, et al., "Establishment in culture of pluripotential cells from mouse embryos", Nature, vol. 292, Jul. 9, 1981, pp. 154–156.

Lin, et al., "Rebombination in mouse L cells between DNA introduced into cells and homologous chromosomal sequences", Proc. Natl. Acad. Sci. USA, vol. 82, pp. 1391–1395, Mar. 1995.

(List continued on next page.)

*Primary Examiner*—Deborah Crouch
(74) *Attorney, Agent, or Firm*—Michael D. Yablonsky; Jack L. Tribble

(57) ABSTRACT

The present invention relates to a transgenic nonhuman animal lacking native amyloid precursor protein. The transgenic mouse of the invention may be used in the study of Alzheimer's Disease and disorders involving the central nervous system.

12 Claims, 9 Drawing Sheets

OTHER PUBLICATIONS

Sandhu, et al., "Expression of the Human B–Amyloid Pro Wagner, et al., "On Transferring Genes Into Stem Cells and Mice", EMBO Journal, vol. 9, No. 10, pp. 3025–3032, 1990.

Wirak, et al., "Deposits of Amyloid B Protein in the Central Nervous System of TransgenicMice", Science, vol. 253, Jul. 19, 1991, pp. 323–325.

Riele, et al., "Highly efficient gene targeting in embryonic stem cells through homologous recombination with isogenic DNA constructs", Proc. Natl. Acad. Sci. USA, vol. 89, 1992, pp. 5128–5132.

Song, et al., "Accurate modification of a chromosomal plasmid by homologous recombination in human cells", Proc. Natl. Acad. Sci. USA, vol. 84, pp. 6820–6824, Oct. 1987.

Smithies, et al., "Insertion of DNA sequences into the human chromosomal B–globulin locus by homologous recombination", Nature, vol. 317, pp. 230–234, 1985.

Sedivy, et al., "Positive genetic selection for gene disruption in mammalian cells by homologous recombination", Proc. Natl. Acad. Sci. USA, vol. 86, pp. 227–231, 1989.

Baribault, rt al., "Embryonic Stem Cell Culture and Gene Targeting in Transgenic Mice", Mol. Biol. Med., 1989, vol. 6, pp. 481–492.

Thomas, et al, "High Frequency Targeting of Genes to Specific Sites in the Mammalian Genome", Cell, vol. 44, Feb. 14, 1986, pp. 419–428.

Thomas, et al., "Site–Directed Mutagenesis by Gene Targeting in Mouse Embryo–Derived Stem Cells", Cell, vol. 51, Nov. 6, 1987, pp. 503–512.

Zheng, et al., "B–Amyloid Precursor Protein–Deficient mice Show Reactive Gliosis and Decreased Locomotor Activity", Cell, vol. 81, 1995, pp. 525–531.

Kawabata, et al., "Amyloid plaques, neurofibrillary tangles and neuronal loss in brains of transgenic mice overexpressing a C–terminal fragment of human amyloid precursor protein", Letters to Nature, vol. 354, Dec. 12, 1991, pp. 476–478.

Bradley, et al., "Formation of germ–line chimaeras from embryo–derived teratocarcinoma cell lines", Nature, vol. 309, 1984, pp. 255–258.

Deng, et al., "Reexamination of Gene Targeting Frequency as a Function of the Extent of Homology between the Targeting Vector and the Target Locus", Molecular and Cellular Biology, Aug. 1992, vol. 12, No. 8, pp. 3365–3371.

Kammesheidt, et al., "Deposition of B/A4 immunoreactivity and neuronal pathology in transgenic mice expressing the carboxyl–terminal fragment of the Alzheimer amyloid precursor in the brain", Proc. Natl. Acad. Sci. USA, vol. 89, Nov. 1992, pp. 10857–10861.

Gossler, et al., "Transgenesis by means of blastocyst–derived embryonic stem cell lines", Proc. Natl. Acad. Sci. USA, vol. 83, Dec. 1986, pp. 9065–9069.

Quon, et al., "Formation of B–amyloid protein deposits in brains of transgenic mice", Nature, vol. 352, Jul. 18, 1991, pp. 239–241.

Dawson, et al., "Age–Related Cognitive Deficits, Impaired Long–Term Potentiation and Reduction in Synaptic Market Density in Mice Lacking the B–Amyloid Precursor Protein", Neuroscience, vol. 90, No. 1, pp. 1–13, 1999.

Ramirez–Solis, et al., "Genomic DNA Microextraction: A Method to Screen Numerous Samples", Analytical Biochemistry, vol. 201, pp. 331–335, 1992.

Evans, et al., "High efficiency vectors for cosmid microcloning and genomic analysis", Gene, vol. 79, pp. 9–20, 1989.

Kim, et al., "Problems encountered in detecting a targeted gene by the polymerase chain reaction", Gene, vol. 103, 1991, pp. 227–233.

Frohman, et al., "Cut, Paste, and Save: New Approaches to Altering Specific Genes in Mice", Cell, vol. 56, Jan. 27, 1989, pp. 145–147.

TRANSGENIC MOUSE HAVING A DISRUPTED AMYLOID PRECURSOR PROTEIN GENE

CROSS-REFERENCE TO RELATED APPLICATION

This is a continuation-in-part of U.S. Ser. No. 08/849,487, filed Jun. 5, 1997, now abandoned and a continuation of PCT/US95/15672, filed Dec. 1, 1995, and a continuation-in-part of U.S. Ser. No. 08/349,334 filed Dec. 5, 1994, now abandoned.

FIELD OF THE INVENTION

The present invention relates to a transgenic nonhuman animal lacking native amyloid precursor protein.

BACKGROUND OF THE INVENTION

Alzheimer's disease (AD) is a neurological disorder that disproportionately affects the population over 65 years of age. Incidence of the disease increases from less than 1% at age 60–65, to 5% at age 75, to as high as 47% at age 85. As a result, 60% to 80% of all cases of dementia in persons over age 65 are caused by AD. Afflicted individuals exhibit impaired cognitive function and memory. Neither a suitable diagnostic procedure nor an effective therapeutic treatment exists for AD. Positive identification of AD requires biopsy or autopsy of the brain.

Although the etiology of AD is unknown, genetic, immunological and environmental factors have been implicated in the development of AD. Distinguishing features of AD include the presence of senile plaques as well as, neurofibrillary tangles and extensive neuronal loss in the neocortex, hippocampus and associated structures. Senile plaques consist of extracellular deposits containing a β-amyloid core surrounded by a halo of dystrophic neurites, glia and astrocytes. β-amyloid deposits are present in neocortex blood vessel walls. The major component of senile plaques is a 4 kDa peptide referred to as Aβ, that is proteolytically cleaved from a larger 120 kDa amyloid precursor protein (APP). Other components of the plaques include ubiquitin, amyloid P, Apo E, interleukin-1, and α-1-antichymotrypsin.

In addition to biochemical evidence supporting Aβ involvement in AD, there are strong genetic data which suggest a link between APP and AD. A clue to the location of a gene involved in AD comes from analysis of Down syndrome patients; in these patients trisomy of chromosome 21 is responsible for the early onset of AD. Karyotype analysis of Down syndrome patients mapped the gene involved to the upper portion of the long arm of chromosome 21. The region involved encodes several genes, including the APP gene. The early onset (~age 35) of AD in Down syndrome patients suggests that an increase in the gene dosage of the responsible marker(s) on the long arm of chromosome 21 may contribute to the neuropathology noticed in most AD patients.

Although the majority of AD cases appear sporadic, several cases of early onset familial AD (FAD) have been reported. Genetic analysis of FAD families has established that the disorder is inherited as a dominant autosomal gene defect, which maps to the long arm of chromosome 21 and is closely linked to the APP gene. These findings are consistent with genetic data obtained from the analysis of Down syndrome patients. Several FAD families have also been identified in which an early onset of AD is strictly correlated with the presence of a mutation in exon 17 of the APP gene at amino acid 717 (Val-Ile). This mutation within the transmembrane spanning domain of the APP cosegregates with FAD. Since the families afflicted with APP717 FAD are of different ethnic origins (English, Japanese and Canadian), evidence for the involvement of the FAD gene in these cases of AD is strong. The mutation is absent from control individuals, in sporadic AD patients, in Down syndrome patients, in late onset familial AD, and also in most other cases of early onset FAD. Several additional mutations in the APP gene have been identified that can explain the occurrence of AD in other FAD families. The genetic evidence in the five distinct early onset APP717 FAD families strongly supports the hypothesis that the APP717 gene in these FAD families is directly positioned in the pathway of AD progression.

The APP gene is approximately 400 kb in length and encodes a glycosylated, transmembrane protein which may be involved in cell-cell interaction. The APP gene has at least 18 exons that create at least 5 distinct APP transcripts by alternative splicing. The predominant transcripts encode proteins of 695, 751 and 770 amino acids (these major forms of APP are referred as APP695, APP751 and APP770, respectively). Transcripts for APP695 are enriched in the brain. Transcripts encoding APP751 and APP770 mRNA species predominate in peripheral tissues. All three isoforms contain the 42 amino acid Aβ domain. APP isoforms 751 and 770 contain an additional 56 amino acid insert encoding the Kuinitz type serine protease inhibitor (KPI). APP is proteolytically metabolized by at least two pathways. One pathway involves an α-secretase cleavage site positioned between Lys 16 and Leu 17 of Aβ domain; proteolytic cleavage at this site precludes the formation of an amyloidogenic Aβ entity. The second pathway produces intact, amyloidogenic Aβ (39–42 amino acids) by proteolytic cleavages at the β- and γ-secretase cleavage sites of the full-length APP molecule.

The Aβ laden senile deposits seen in AD patients are also found in aged humans and other aged mammals including non-human primates, polar bears and dogs. However, other aged mammals, such as laboratory rats and mice, do not normally develop Aβ deposits. This could be due to the fact that the three amino acid differences present in the β-amyloid sequence between human and mouse APP prevents mouse Aβ from forming plaques. The lack of a cost-effective, experimental animal model mimicking human pathogenesis hinders the understanding AD neuropathology and developing therapeutics against AD.

Transgenic technology may offer a suitable alternative to this problem. Addition of a gene construct directing high levels of human APP or its components to key regions in the murine central nervous system may cause neuropathological changes resembling the AD phenotype. Attempts to express human amyloid precursor protein segments or the full-length wild type protein in transgenic animals have been successful. Numerous reports exist outlining expression of different wildtype, full-length and truncated APP cDNA isoforms in mouse (Kammesheidt et al., (1992) *Proc. Natl. Acad. Sci.,* 89, 10857–10861; Sandhu et al., (1991) *J. Biol. Chem.,* 266, 21331–21334; Quon, et al., (1991) *Nature,* 352, 239–241; Wirak et al., (1991) *Science,* 253, 323–325; Kawabata et al., (1991) *Nature* 3, 476–478; Patent, International publication number WO93/02189, Neve, R., Inventor). However, these previous attempts to generate transgenic mouse models for AD have essentially failed. This failure could have been caused by the presence of the endogenous mouse APP gene in the transgenic mouse, which "protects" the human βA4 from depositing in the mouse brain.

Accordingly, it is an object of the present invention to provide a transgenic mouse which does not express mouse amyloid precursor protein. The transgenic mice of the present invention are useful in the determination of the in vivo function of APP and the β-amyloid peptide in the central nervous system and in other tissues. These mice are being bred with transgenic mice expressing the human APP FAD with the aim of producing a strain of mice in which the only APP produced is of human origin.

The precise roles of APP in AD is not fully understood at this time. Due to the biological importance of APP in AD and other neurological disorders, the APP gene is an important target for embryonic stem (ES) cell manipulation.

The generation of APP deficient transgenic mice would aid in defining the normal role(s) of APP, and allow an animal model of APP deficiency to be used in the design and assessment of various approaches to modulating APP activity. Such APP modified transgenic mice can also be used as a source of cells for cell culture.

SUMMARY OF THE INVENTION

The present invention relates to a transgenic nonhuman animal lacking native amyloid precursor protein (APP). The transgenic mouse of the invention may be used in the study of Alzheimer's Disease and disorders involving the central nervous system.

The targeting vector (pHZ038) contains from left to right: 1.4 kb of 5' homology with the APP locus; a PGKneo expression cassette inserted in the opposite orientation to the APP gene; a fragment of 7.1 kb homologous to the 3' part of the APP promoter region; and an MC1-TK gene. A 3.8 kb sequence containing the 1.0 kb APP promoter, the first exon and part of the first intron was deleted. The homologies of the endogenous APP gene and the targeting vector are represented as shaded rectangles. Targeted recombination between the vector and the wild-type APP locus results in the deletion of the promoter and exon 1 of the APP gene followed by its replacement with a 1.5 kb neo coding sequence. The probes used for Southern blot analysis were the 1.0 kb XbaI-BglII fragment (5'-probe), the 0.8 kb BglII-NcoI fragment (3'-probe), both of which are outside the targeting vector, and the neo sequence. EcoRI was used to differentiate the wild-type and the targeted APP alleles, which generates a 9.0 kb and 6.5 kb fragments by the 5'-probe and a 9.5 kb and a 9.0 kb by the 3'-probe, respectively. R: EcoRI, X: XbaI, B: BglII, N: NcoI. Pr: mouse APP promoter, El: exon 1 of the mouse APP gene. PGK: phosphoglycerate kinase promoter.

Figure 3A:
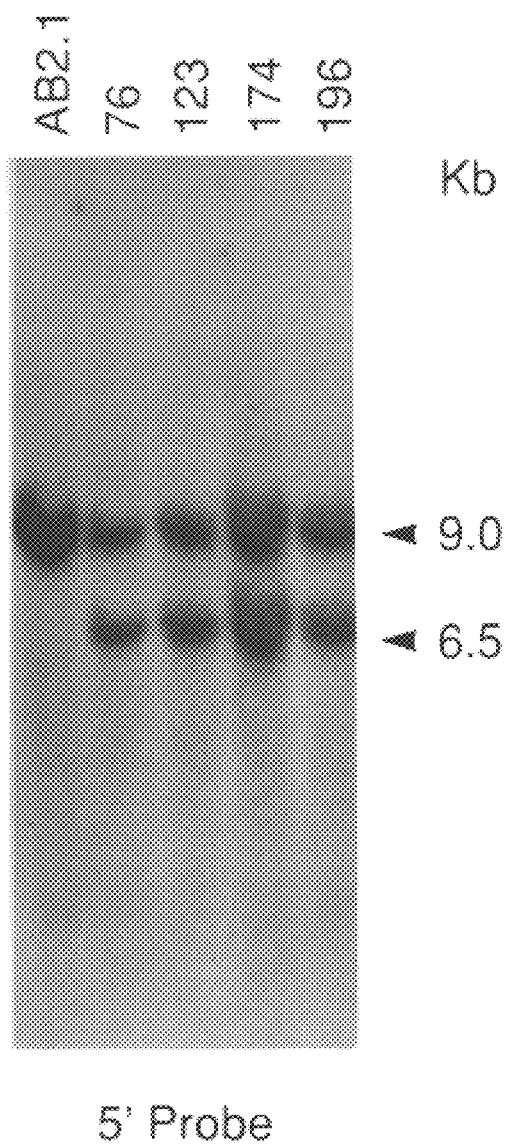
Figure 3B:
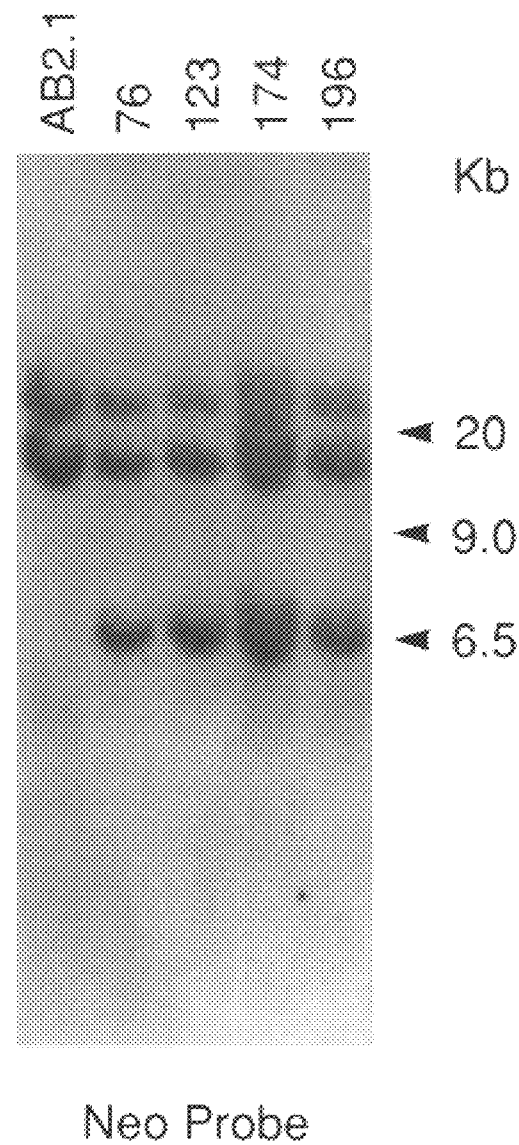

FIG. 3 is a Southern hybridization analysis of four targeted embryonic stem (ES) clones having an APP knockout.

ES cell DNA (8 μg) from the wild-type AB2.1 cells and four positive clones (76, 123, 174 and 196) were restriction enzyme digested with EcoRI, electrophoresed on a 0.7% agarose gel, transferred onto a Gene Screen Plus nylon membrane (NEN-Dupont) and hybridized with a 5'-probe (labeled a) a 3'-probe (data not shown), and a neo probe (labeled b) A 6.5 kb diagnostic fragment is detected by the 5'-probe in all the targeted clones in addition to the wild-type 9.0 kb fragment. Probing of the same filter with a neo coding sequence (b) shows that the neo gene is present in the 6.5 kb band and is the only integration event in all the clones. The other two bands at high molecular weight corresponds to a nonfunctional neo sequence introduced by a retrovirus in the parental AB2.1 cells.

Figure 4:
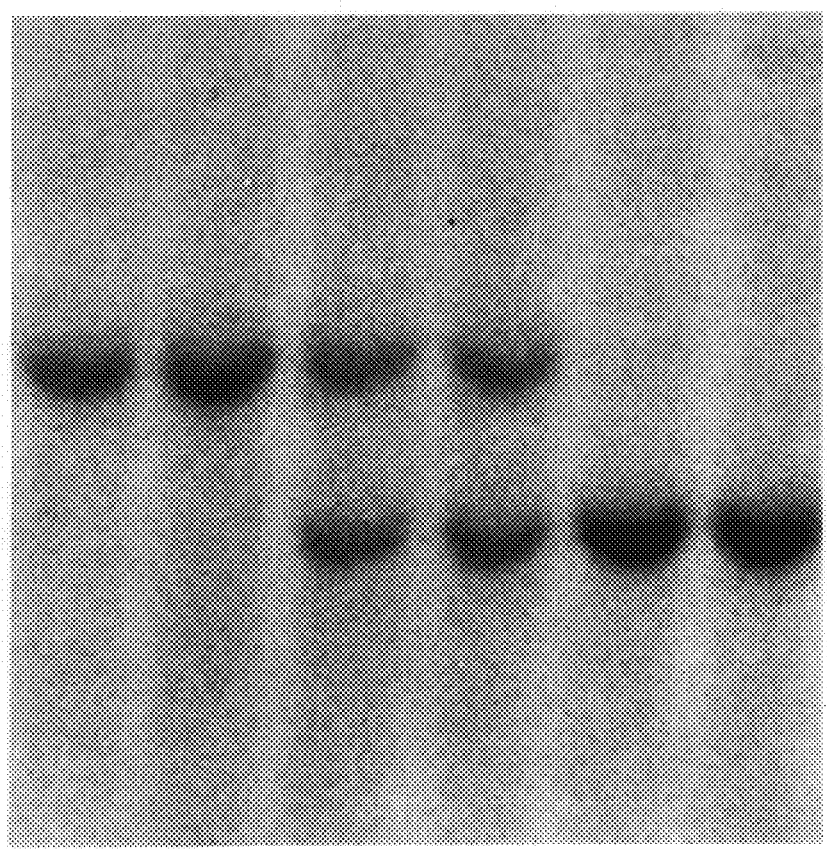

FIG. 4 is a Southern hybridization analysis of tail DNA from transgenic mice having an APP knockout. Southern analysis of genomic DNA from het. x het. crosses yielded the expected number of mice homozygous for the disrupted APP allele.

Genomic DNA isolated from the tails of two week old pups generated from crosses of heterozygous mice was digested with EcoRI, blotted onto filters, and hybridized with the 5'-probe. +/+: wild-type; +/–: heterozygotes; –/–: homozygous APP deficient mice.

Figure 5:
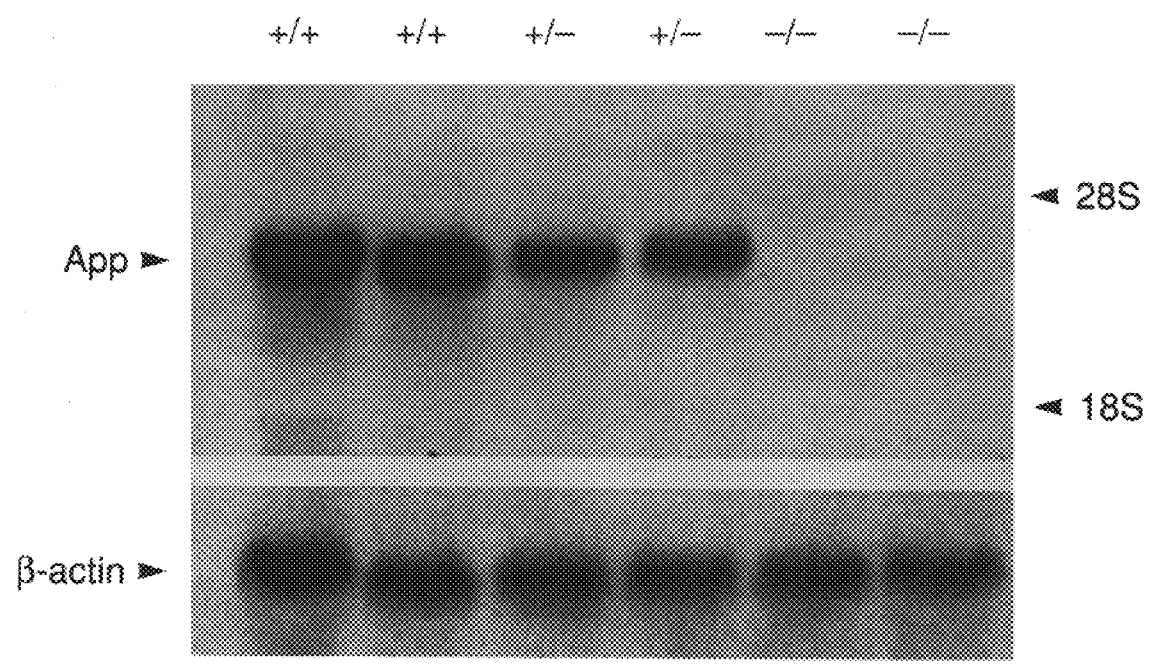

FIG. 5 is a Northern hybridization analysis for the determination of APP transcripts in the knockout and wild-type control mice. As expected, the brain RNA from the knockout mice did not exhibit any detectable APP expression, whereas wild-type control and heterozygous animals showed a significant amount of APP activity.

Total RNA (20 μg) from wild-type (+/+), heterozygous (+/–) and homozygous (–/–) APP mice were isolated (2 mice each) from brain using the RNAzol B method (Biotecx Laboratories, Inc.) and probed with an APP695 cDNA probe. The lower panel shown in each case is a control hybridization with mouse β-actin cDNA to show that identical amounts of RNA were loaded in each lane.

Figure 6A:
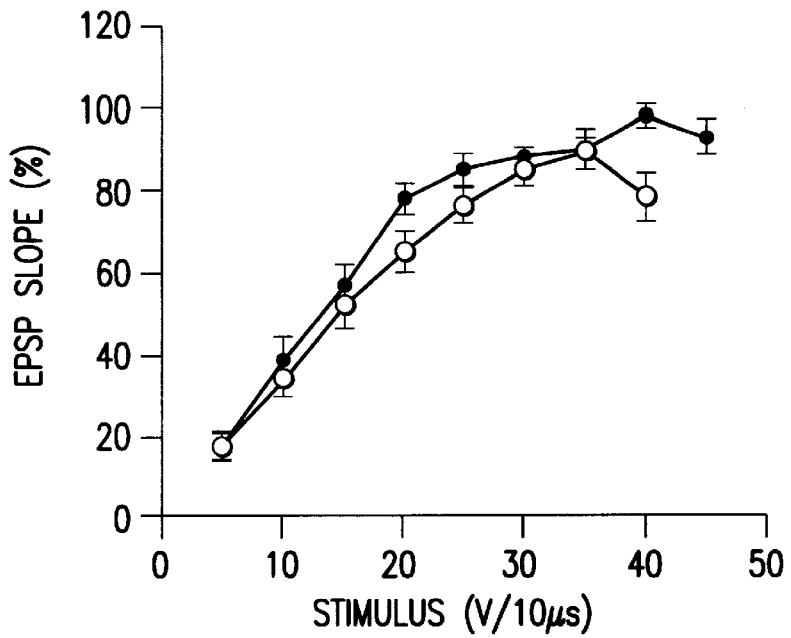
Figure 6B:
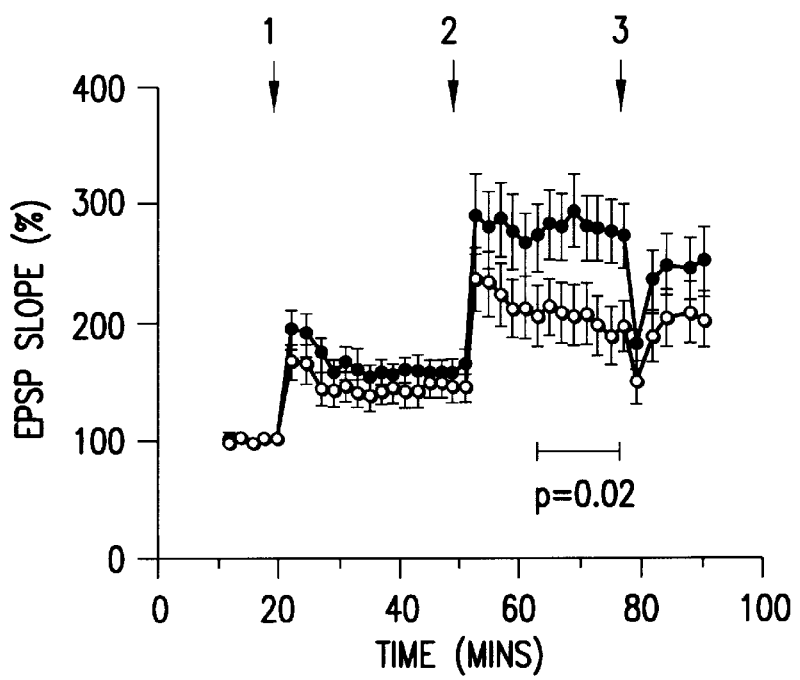
Figure 6C:
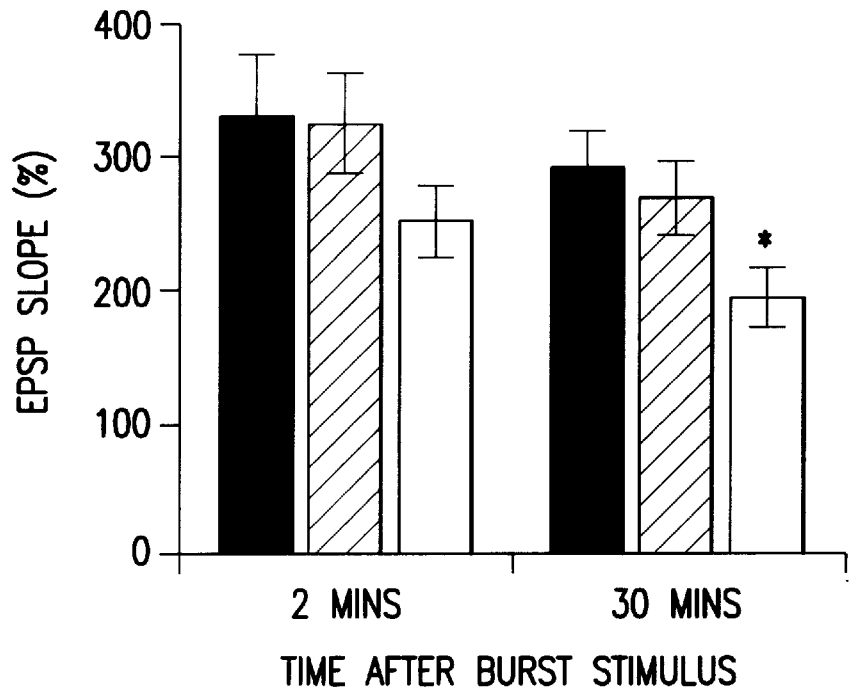
Figure 6D:
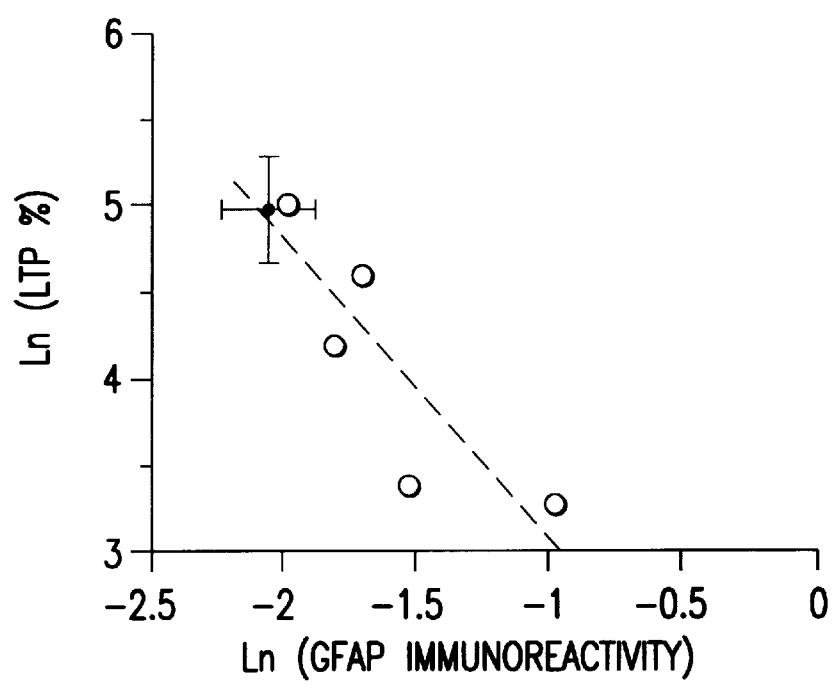

FIGS. 6A–6D are graphs showing stimulus dependent increases in synaptic efficacy in CA1 region of the hippocampus are suppressed in mice (eight to twelve months old) deficient in β-amyloid precursor protein, APP. FIG. 6A: Stimulus-response curves in tissue from APP-null mice (open circles) were comparable to that in control isogenic mice (filled circles). Each point represents the mean (±SEM) of the population excitatory post synaptic potential (EPSP) slope expressed as a percentage of the maximum from 26 and 21 slices respectively. The peak EPSP slope was not significantly different between APP-null (0.84±0.17 mV/ms) and wild-type mice (0.97±0.23 mV/ms). FIG. 6B: Post-tetanic increases in synaptic efficacy induced by the threshold stimulus (arrow 1; 10 events at 100 Hz) were not markedly affected; however the increase following the burst stimulus paradigm (4×10 at 100 Hz) was significantly attenuated (P=0.024, F=5.59 with 1,36 degrees of freedom; ANOVA on Ln transformed data 10 to 30 min after burst stimulus). Short term depotentiation induced by 100 stimuli at 1 Hz (arrow 3) was not markedly different between the wild-type controls (filled circles) and APP-null mice (open circles). Data are from 18 brain slices from seven APP-null mice, and 20 brain slices from six wild type mice. FIG. 6C: The potentiation of EPSPs following the burst stimulus paradigm (arrow 2 in FIG. 6B) was normal in wild-type mice (hatched bars) compared to tissue from a control C57 mouse strain (filled bars); however in the APP-null mice (open bars) the decrease in synaptic efficacy was observed immediately, and sustained for up to 30 min after the burst stimulus. FIG. 6D: The deficit in LTP formation, assessed 30 min after the burst stimulus, was significantly correlated with the increase in GFAP immunoreactivity in the contralateral hippocampus taken from each animal for electrophysiological studies ($r^2<0.79$, P<0.02). Open circles represent mean LTP formation in two to four brain slices from each of from 5 different APP-null animals). The filled circle represents the mean increase in EPSP slope in a subpopulation of wild-type control mice that were also assessed for GFAP immunoreactivity (n=4 wild-type animals). (From FIG. 1 of Dawson, G. R., et al., (1999) Neuroscience 90(1):1–13; which publication is incorporated by reference herein in its entirety.)

Figure 7A:
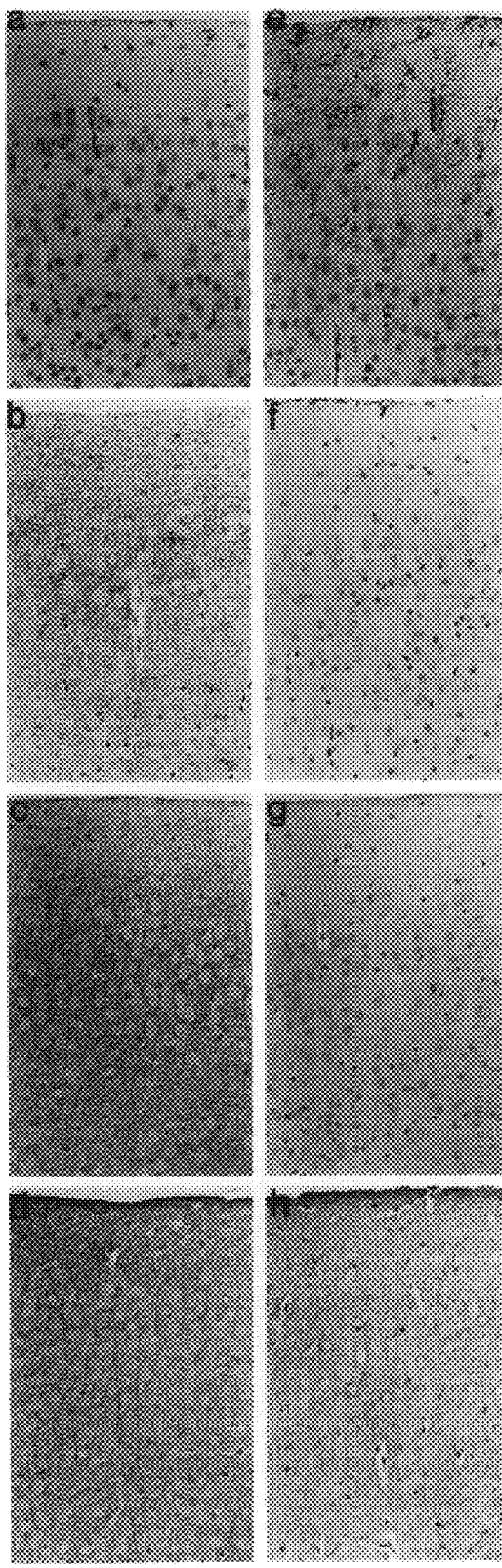
Figure 7B:
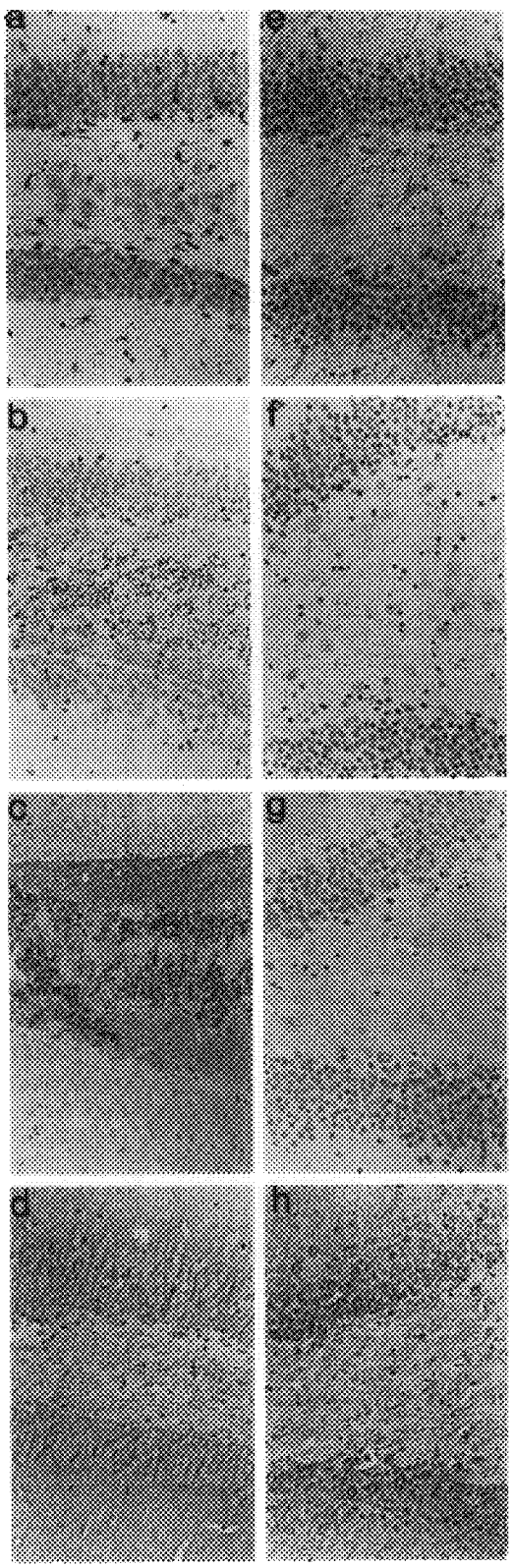

FIGS. 7A–7B are photographs showing representative immunostaining patterns for GFAP, synaptophysin, synapsin and MAP-2 in the frontal cortex (FIG. 7A) and hippocampus (FIG. 7B) of wild-type and APP-null mice. In the frontal cortex (FIG. 7A) there was a marked increase in the number of GFAP-labelled reactive astrocytes (panel e) and a marked decrease in synaptophysin (panel f), synapsin (panel g) and MAP-2 (panel h) immunoreactivities in the APP-null mice compared with the immunostaining patterns (panels a, b, c, and d respectively) of wild-type mice. Note the MAP-2-stained long apical dendrites originating from layer V pyramidal neurons in the wild-type mice (panel d) and an almost complete loss in the APP-null mice (panel h). (Scale bar= 100 um) In the hippocampus of APP-null mice (FIG. 7B) there was a pronounced increase in the number of reactive astrocytes (panel e) and marked decreases in synaptophysin (panel f), synapsin (panel g) and MAP-2 (panel h) immunoreactivities compared with the patterns seen in the wild-type mice (panels a, b, c, and d respectively). The decreases in synaptophysin and synapsin immunoreactivities was most dramatic in the hilus of the dentate gyrus and CA3 region of the hippocampus (panels g and h). The MAP-2 staining shows a decreased branching of dendrites in the hippocampus especially in the molecular layer of the dentate and in the CA3 region (panel f). Note the accumulation of MAP-2 immunoreactivity in cell bodies of the dentate granule cells and CA1 pyramidal cells as a result of the dendritic loss. (Scale bar=100 um) (From FIG. 2 of Dawson, G. R., et al., (1999) Neuroscience 90(1):1–13)

DETAILED DESCRIPTION OF THE INVENTION

The present invention relates to a transgenic nonhuman animal lacking native amyloid precursor protein. The transgenic mouse of the invention may be used in the study of Alzheimer's Disease and disorders involving the central nervous system.

A 39 to 43 amino acid β-amyloid peptide is the major component of the neuritic plaques characterizing Alzheimer disease. β-amyloid is derived from a larger amyloid precursor protein (APP). The APP mRNA undergoes alternative splicing to generate several isoforms, encoding proteins that range from 695 to 770 amino acid residues. Among these, APP695 is expressed predominantly in neurons and APP751 and APP770 can be detected in all the tissues examined. Five different types of point mutations have now been identified in the human APP gene, causative of familial early onset Alzheimer's disease (FAD) in several unrelated families. These affected families provide the strongest evidence yet for the notion that APP processing and the β-amyloid peptide serve a central role in Alzheimer disease progression.

APP is one of the most abundant proteins in the brain and the β-amyloid peptide is secreted in cerebrospinal fluid (CSF) of healthy individuals and AD patients. The functions of the APP and β-amyloid in vivo are obscure. The APP has been implicated as a growth factor in vitro in fibroblast cultures. The β-amyloid peptide has been shown to have neuroprotective and neurotoxic actions, dependent on the cell line and protein preparations tested. A Kunitz protease inhibitor domain in the N-terminal portion of the APP may serve a role in regulating protein half-life.

We wished to inactivate the APP gene in order to evaluate its role in mouse development and in the central nervous system. In addition, in order to generate a murine model of FAD, APP deficient mice may be useful as acceptors of the human FAD protein. Mouse APP is overall conserved when compared to human APP but differs in three potentially essential amino acid residues of the β-amyloid domain. The murine APP gene is about 400 kb in size and is encoded by at least 18 exons. The murine APP gene was inactivated by deleting its promoter and first exon, which encodes the ATG translation initiation codon. To target the APP gene in murine ES cells, a positive-negative selection strategy was used. The targeting vector pHZ038 (FIG. 2) encoded 8.5 kilobases (kb) of DNA derived from the 5' end of the APP gene. A 3.8 kb sequence encoding the APP promoter and the first intron was deleted from this vector and replaced with a positive selectable marker, PGKneo (neomycin-phosphotransferase). A MC1-TK (thymidine kinase) cassette (labeled HSV-TK in FIG. 2) was inserted at the end of the vector for negative selection. Correct homologous recombination between the targeting vector and one of the APP alleles in the ES cells would result in a deletion of the APP promoter and exon 1, encoding the signal peptide.

The targeting vector was electroporated into AB2.1 ES cells. G418 and FIAU resistant clones were screened by a mini-Southern protocol. A five-fold enrichment was achieved by selecting the cells with FIAU. Six targeted clones were identified and the frequency of targeted recombination versus random integration at the APP locus was 1/160 (FIG. 3). Of four clones injected into blastoysts two (no. 76 and 174) transmitted the targeted APP allele to the offspring. Heterozygous matings were set up to produce mice homozygous for the disrupted APP gene.

Homozygous APP knockout mice that resulted from these breedings were generated at expected frequencies (FIG. 4). These mice appeared normal and healthy up to 14 weeks of age. Northern blot analysis of RNA isolated from brain using APP695 cDNA as a probe showed that APP mRNA was not produced in mice homozygous for the targeted allele. The APP mRNA level was reduced by approximately 50% in the heterozygous mice as compared to wild-type controls (FIG. 5).

The present invention utilizes a cloned DNA encoding the 5' portion of the APP gene. Transgenic animals are generated which have an altered APP gene. The alterations to the naturally occurring gene are modifications, deletions and substitutions. Modifications, deletions and substituteions may render the naturally occurring gene nonfunctional, producing a "knockout" animal, or may lead to an APP with altered function. These transgenic animals are critical for drug antagonist or agonist studies, for creation of animal models of human diseases, and for eventual treatment of disorders or diseases associated with APP. Transgenic animals lacking native APP are useful in characterizing the in vivo function of APP. A transgenic animal carrying a "knockout" of APP is useful for the establishment of a nonhuman model for diseases involving APP, and to distinguish between the activities of APP in in vivo and in vitro systems.

The term "animal" is used herein to include all vertebrate animals, except humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule may be integrated within a chromosome, or it may be extra-chromosomally replicating DNA. The term "germ cell-line transgenic animal" refers to a transgenic animal in which the genetic information was introduced into a germ line cell, thereby conferring the ability to transfer the information to offspring. If such offspring in fact possess some or all of that information, then they, too, are transgenic animals.

The genetic alteration or genetic information may be foreign to the species of animal to which the recipient belongs, or foreign only to the particular individual recipient. In the last case, the altered or introduced gene may be expressed differently than the native gene.

The altered APP gene should not fully encode the same APP as native to the host animal, and its expression product should be altered to a minor or great degree, or absent altogether. However, it is conceivable that a more modestly modified APP gene fall within the scope of the present invention.

A type of target cell for transgene introduction is the embryonal stem cell (ES). ES cells may be obtained from preimplantation embryos cultured in vitro and fused with embryos (M. J. Evans et al., Nature 292: 154–156 (1981); Bradley et al., Nature 309: 255–258 (1984); Gossler et al. Proc. Natl. Acad. Sci. USA 83: 9065–9069 (1986); and Robertson et al., Nature 322, 445–448 (1986)). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (R. Jaenisch, Science 240: 1468–1474 (1988)).

Since the proposed APP functions are complex, they must be examined in a variety of ways. One approach to the problem of determining the contributions of individual genes and their expression products is to use isolated genes to selectively inactivate the native wild-type gene in totipotent ES cells (such as those described herein) and then generate transgenic mice. The use of gene-targeted ES cells in the generation of gene-targeted transgenic mice was described 1987 (Thomas et al., Cell 51:503–512, (1987)) and is reviewed elsewhere (Frohman et al., Cell 56:145–147 (1989); Capecchi, Trends in Genet. 5:70–76 (1989); Baribault et al., Mol. Biol. Med. 6:481–492, (1989); Wagner, EMBO J. 9: 3025–3032 (1990); Bradley et al., Bio/Technology 10: 534–539 (1992)).

Techniques are available to inactivate or alter any genetic region to any mutation desired by using targeted homologous recombination to insert specific changes into chromosomal alleles. However, in comparison with homologous extrachromosomal recombination, which occurs at frequencies approaching 100% homologous plasmid-chromosome recombination was originally reported to only be detected at frequencies between $10^{-6}$ and $10^{-3}$ (Lin et al., Proc. Natl. Acad. Sci. USA 82:1391–1395 (1985); Smithies et al., Nature 317: 230–234 (1985); Thomas et al., Cell 44:419–428, (1986); Song et al., Proc. Natl. Acad. Sci. USA 84:6820–6824 (1987)). Nonhomologous plasmid-chromosome interactions are more frequent, occurring at levels $10^5$-fold (Lin et al., Proc. Natl. Acad. Sci. USA 82:1391–1395 (1985)) to $10^2$-fold (Thomas et al., Cell 44:419–428 (1986); Song et al., Proc. Natl. Acad. Sci. USA 84:6820–6824 (1987)) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., Nucleic Acids Res. 16:8887–8903 (1988); Kim et al, Gene 103:227–233 (1991)). Alternatively, a positive genetic selection approach has been developed in which a marker gene is constructed which will only be active if homologous insertion occurs, allowing these recombinants to be selected directly (Sedivy et al., Proc. Natl. Acad. Sci. USA 86:227–231 (1989)). One of the most general approaches developed for selecting homologous recombinants is the positive-negative selection (PNS) method developed for genes (such as APP) for which no direct selection of the alteration exists (Mansour et al., Nature 336:348–352: (1988); Capecchi, Science 244:1288–1292, (1989); Capecchi, Trends in Genet. 5:70–76 (1989)). The PNS method is more efficient for targeting genes which are not expressed at high levels because the marker gene has its own promoter. Nonhomologous recombinants are selected against by using the Herpes Simplex virus thymidine kinase (HSV-TK) gene and selecting against its nonhomologous insertion with the herpes drugs such as gancyclovir (GANC) or FIAU (1-(2-deoxy 2-fluoro-B-D-arabinofluranosyl)-5-iodouracil). By this counter-selection, the number of homologous recombinants in the surviving transformants can be enriched.

As used herein, a "targeted gene" or "Knock-out" (KO) is a DNA sequence introduced into the germline of a non-human animal by way of human intervention, including but not limited to, the above described methods. The targeted genes of the invention include DNA sequences which are designed to specifically alter cognate endogenouos alleles.

The methods for evaluating the targeted recombination events as well as the resulting knockout mice are readily available and known in the art. Such methods include, but are not limited to DNA (Southern) hybridization to detect the targeted allele, polymerase chain reaction (PCR), polyacrylamide gel electrophoresis (PAGE) and Western blots to detect DNA, RNA and protein.

The following is presented by the way of examples and is not to be construed as a limitation on the scope of the invention:

EXAMPLE 1

Preparation of a Murine Embryonic Stem Cell Lenomic Library

Evidence suggested that homologous genomic targeting in embryonic stem (ES) cells is strongly inhibited (>100x) by subtle base-pair differences in their genomic DNAs (Riele et al., Proc. Natl. Acad. Sci. USA 89:5128–5132 (1992); Deng et al., Mol. Cell. Biol. 12:3365–3371 (1992)). To circumvent this potential problem, genomic libraries were constructed from ES cells grown in the absence of feeder cell layers for the isolation of genes to be used for subsequent ES cell targeting.

Genomic libraries were prepared from AB2.1 cells according to the in situ procedure described in (Mudgett et al., Genomics 8:623–633, (1990)). The cosmid vector sCos- 1was chosen, as it allows both the vector and the insert to be dephosphorylated. This prevents concantamer formation and generally results in genomic libraries of better quality and quantity (up to $5\times10^6$ clones per package) than is achieved with other vectors (Evans et al., Gene 79:9–20, (1989)).

The genomic library was constructed with bacterial hosts SURE. The SURE host line (Stratagene) was used to stably maintain indirect repeats and allow isolation of methylated DNA.

EXAMPLE 2

Isolation and Characterization of Mouse APP Cosmid Clone

The primary mouse cosmid library of Example 1 was screened using a 1.0 kb HindIII-PvuII fragment located in the promoter of the APP gene as a probe (Izumi et al, Gene 112: 189–195 (1992)). The conditions for library plating and screening are described by Sambrook et al. in "Molecular cloning: A Laboratory Manual". Cold Spring Harbor Press, (1989). About $6\times10^4$ clones were plated onto a 150 mm NZYDT/amp (100 µg/ml) plate. A total of $1.2\times10^6$ independent clones were screened. To reduce the chance of false positives, duplicate lifting was used. The hybridization and washing conditions were maintained at high stringency to reduce the chance of isolating different but homologous genes and related pseudogenes. Only one positive clone was identified which was further purified through secondary and tertiary screenings. The cosmid DNA was prepared using standard conditions (Sambrook et al. supra).

Figure 1:
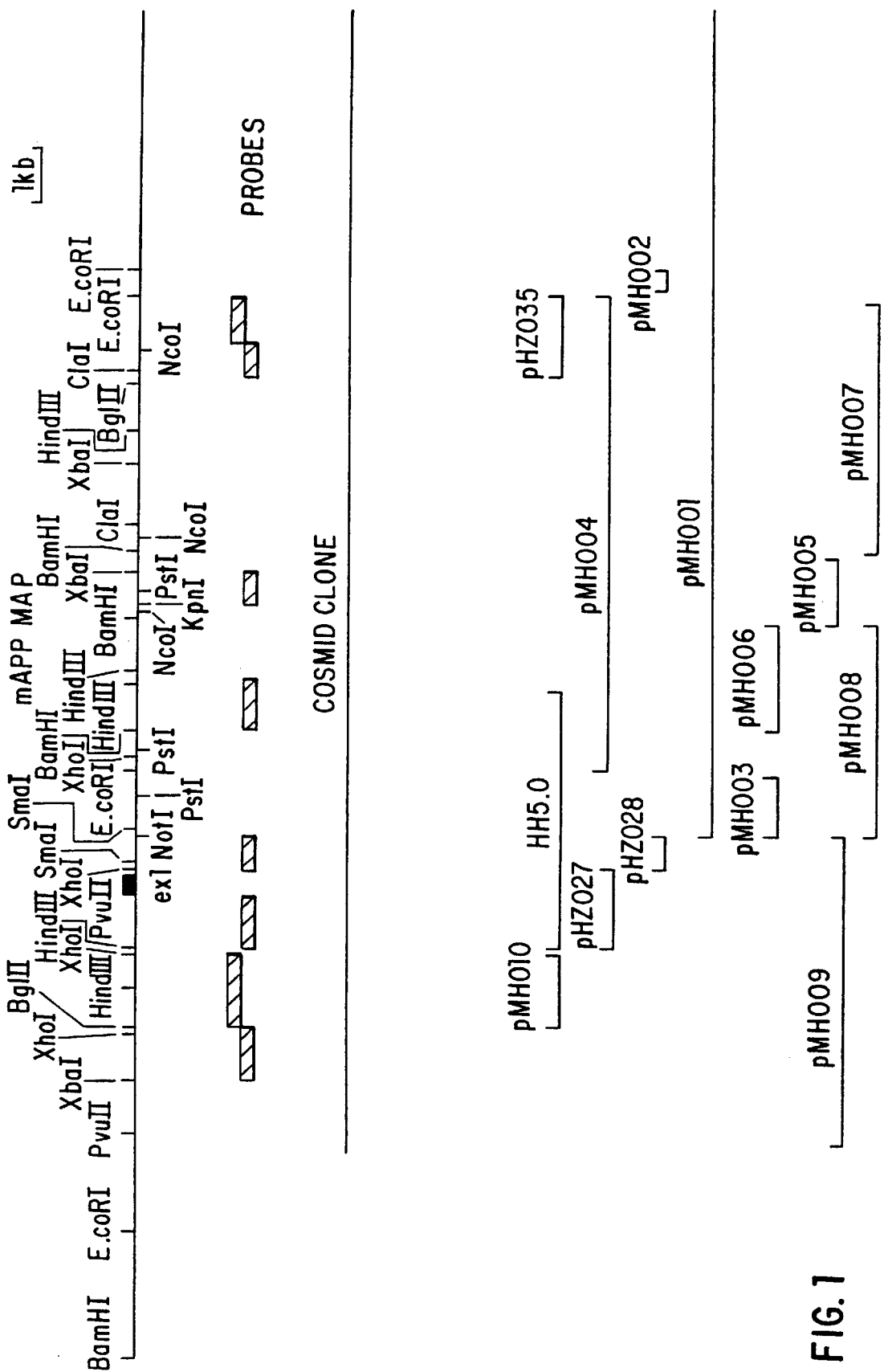
FIG. 1 is a genomic map of the mouse APP gene, the location of the cosmid clone isolated from a primary genomic library and different probes and subclones generated from the cosmid clone. ex 1: exon 1 of the APP gene.

The cosmid DNA was digested with different restriction endonucleases, electrophoresed on agarose gels, and hybridized with different probes isolated from the plasmid HH5.0 (Izumi et al., Gene 112: 189–195 (1992)) to map the boundary as well as the promoter and exon 1 of the mouse APP gene (FIG. 1).

EXAMPLE 3

Construction of APP Gene Targeting Vector

From the knowledge of the genomic organization of mouse APP gene with regard to restriction sites, promoter and the first exon (Example 2), a gene targeting vector for inactivating the APP gene was prepared using standard cloning techniques (Sambrook et al., supra):

a) A three-way ligation was performed using the 1.4 kb BglII-XhoI fragment in the 5' portion of the APP cosmid clone upstream of exon 1 (ex 1), the 7 kb XhoI-BglII fragment in the 3' portion of the cosmid clone, and BamHI digested pKS vector. The resulting plasmid was named pHZ036.

b) Plasmid pHZ036 was partially-digested with XhoI and ligated with the 1.5 kb XhoI-SalI fragment of PGKneo. A ligation product with neo inserted in between the two APP fragments was selected and referred to as pHZ037.

c) A 2 kb XhoI fragment from pKS-TK was inserted into the SalI digested pHZ037 vector. The resulting plasmid, pHZ038, is the complete construct for targeting of the mouse APP gene.

EXAMPLE 4

Targeted Disruption of the APP Gene in Murine ES Cells

Figure 2:
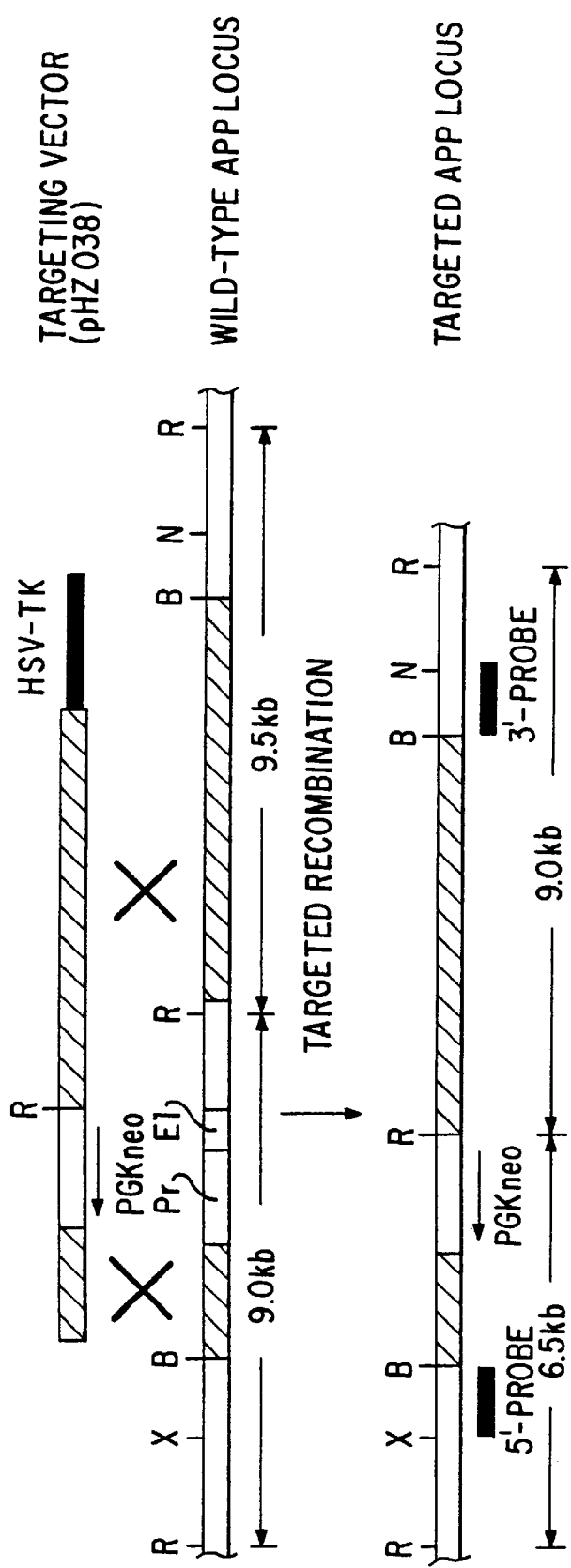
FIG. 2 is the predicted modification of the mouse chromosomal APP gene by targeted recombination using replacement vector pHZ 038.

The targeting vector used in the APP gene disruption experiments was the pHZ038 vector of Example 3. When this vector recombined with the wild-type APP allele to generate the APP knockout (APP KO), the promoter and exon 1 of the APP gene encoding the ATG translation iniation codon and the signal peptide were deleted (FIG. 2). The mouse embryonic stem cell line AB2.1 was electroporated with NotI digested pHZ038 to linearize the plasmid, leaving the pks sequence attached to the end of the TK cassette. All AB2.1 ES cells were cultured on SNL feeder cells as described (Robertson, in Teratocarcinomas and embryonic stem cells, IRL Press, pp. 71–112 (1987)). Electroporations were performed with $1\times10^7$ ES cells and 25 µg linearized vector in 0.8 ml PBS buffer at 230v, 500 µF using a Bio-Rad Gene Pulser. ES cell transformants were selected with the antibiotic geneticin (Gibco G418: 200 µg/ml active G418) 24 hr post electroporation, and some transformants were counter-selected with FIAU (Bristol Myers Squibb; 0.4 µM) 48 hours later for enhancement of homologous recombinants. Murine leukemia inhibitory factor (LIF; ESGRO, Gibco BRL, Inc.) was used at 200 U/ml. Selection with FIAU resulted in about five-fold fewer colonies as compared to G418 selection alone, thereby enhancing the isolation of targeted transformants. G418- and FIAU-resistant ES clones were isolated, grown up and analyzed by a mini-Southern protocol (Ramirez-Solis, R. et al. Anal. Biochem. 201:331–335, 1992). A total of six targeted clones were identified from 200 double resistant colonies analyzed. Therefore, the frequency of targeted recombination vs. random integration at the APP locus is 1/160. Detailed Southern blot analysis of the targeted clones using 5'-, 3' and neo probes showed the expected integration pattern both within the APP gene and in the APP flanking region. Integration events other than the targeted recombination could not be detected.

EXAMPLE 5

Injection of APP KO Clones into Donor Blastocysts

All APP-targeted AB2.1 cell lines were characterized by Southern hybridization analysis to confirm that APP was disrupted. Targeted cell lines which grew normally and did not contain an abnormal proportion of differentiated cells (Robertson, in supra) were then separated from their feeder cells by treating the cell culture with trypsin, allowing the feeder cells to attach for about 30 min, and removing the unattached ES cells. The ES cells were injected into recipient blastocysts. Four APP targeted ES clones (76, 123, 174 & 196) were injected into C57BL/6J recipient blastocysts in separate experiments using techniques described previously (Bradley, A. "Production and analysis of chimeric mice. In Teratocarcinomas and Embryonic Stem Cells: A Practical Approach", E. J. Robertson, ed.Oxford:IRL Press, (1987), pp113–151). The injected C57Bl/6J recipient blastocysts were reimplanted into the uteri of day 3 pseudopregnant Tac:SW(fBR) mice and allowed to develop to term. Progeny were screened initially by coat color chimerism, the agouti color (which is the ES cell background strain) being an indicator of ES cell chimerism. APP targeting was confirmed by Southern hybridization analysis performed on genomic DNA isolated from tail samples obtained from these mice.

Injection of the APP targeted lines yielded 12 male chimeras and one female chimera, with the chimerism ranging from 20% to 100%. As the ES cell line AB2.1 is homozygous for the agouti (A) coat color gene, penetrance of ES cells into the injected (black coat color) C57Bl/6 blastocyst gives rise to chimeric coat color mice.

EXAMPLE 6

Breeding Chimeric Mice

The chimeric coat color mice were bred to wild-type C57BL/6 (black coated) and 129/J (agouti coated) female mice. Some of the progeny from the chimera X C57BL/6 cross were expected to be agouti if the chimeric male had ES cell genetic material incorporated into its germline (agouti is dominant to black coat color). The chimera X 129/J cross would yield only agouti mice. These crosses were performed to transfer ES cell genetic information, including the disrupted APP allele, to its offspring. Breeding of three male chimeras from both clone 76 and 174 resulted in agouti pups when crossed with C57Bl/6J females.

To determine the APP genotypes, genomic DNA was purified from about 1 cm of tail taken from each mouse at about two weeks of age. The genomic DNA was isolated as described (Laird et al., supra), followed by phenol:chloroform extractions and ethanol precipitation. Southern hybridization analysis (as described in Example 5) were used to identify offspring which contained the disrupted APP allele. These transgenic offspring were heterozygous for the APP disruption. Both transgenic heterozygous and nontransgenic mouse (tail) genomic DNAs were digested with EcoRI, and were hybridized with 5' flanking DNA probe to confirm the transgenic APP structure. Southern hybridization analysis confirmed that the structure of the altered APP allele was identical to that predicted, and previously characterized in the APP targeted ES clones.

EXAMPLE 7

Breeding Heterozygous Mice and Generation of Homozygous APP Deficient Mice

Male and female transgenic mice, each of which contained one copy of the altered APP allele (heterozygous mice), were mated with each other to generate mice in which both copies of the APP gene encoded the targeted, altered APP allele. It was predicted that one fourth of the mouse embryos would be homozygous for the altered APP gene. Surviving offspring were genotyped by Southern hybridization as described above (FIG. 4). It was determined that 21 (24%) of the 87 offspring mice were homozygous APP−/−, 30 (34%) were wild-type APP+/+, and 36 (41%) were heterozygous APP+/−. These numbers indicate that there was no significant decrease in the number of APP deficient transgenic mice which survived at two weeks of age.

EXAMPLE 8

Characterization of Homozygous APP Deficient Mice

Surviving homozygous APP deficient mice of Example 7 were bred with wild-type or heterozygous mates to determine if they were fertile. All homozygous APP−/− males and females tested were fertile. Significant differences in gross morphology or histology between the APP deficient mice and the wild-type or heterozygous mice were not observed.

A combination of electrophysiological and immunohistochemical procedures were used to evaluate mice deficient in the APP gene.

EXAMPLE 9

Confirmation of APP Inactivation by Northern Analysis

Total brain RNA was prepared from the wild-type, heterozygous and homozygous APP KO mice. Northern hybridizations were carried out by standard procedures using APP695 cDNA as a probe (FIG. 5). No RNA was detected in the two homozygous APP knockout mice.

EXAMPLE 10

Cell Culture

The transgenic animals of the invention may be used as a source of cells for cell culture. Cells of brain tissues lacking the APP gene may be cultured using standard culture techniques.

EXAMPLE 11

Measurement of Long-Term Potentiation

To determine whether APP gene deletion affected synaptic processes that are thought to contribute to memory formation, the formation of long-term potentiation (LTP) within the CA1 region of the hippocampus was examined. The results from electrophysiological and immunohistochemical procedures, using mice with ages between eight to twelve months, revealed an impairment in LTP and a pronounced decrease in the density of several presynaptic vesicle marker proteins in APP-null mice compared to the wild-type controls.

Extracellular microelectrode recordings were made from the stratum radiatum of the CA1 region in mouse hippocampal brain slices and excitatory postsynaptic potentials (EPSPs) were elicited by stimulation of the Schaffer collateral commisural pathway with bipolar stimulating electrodes (0.033 Hz; Seabrook G. R, et al. (1997) Neuropharmacology 36(6):823–830). EPSPs were elicited at a constant, sub-threshold stimulus intensity which provided a minimum capacity for potentiation of five-fold. In tissue from both the wild-type controls and APP-null mice this was 19±1% (n=20 and 18 respectively) that of the stimulus intensity which evoked the maximal EPSP amplitude.

The ability of high frequency stimuli to induce LTP in tissue from APP-null mice (eight to twelve months-old) and an isogenic wild-type control strain were compared to that from a control C57 mouse strain (eight to twelve months-old). Three stimulus paradigms were used: (i) a threshold stimulus consisting of 10 events at 100 Hz; (ii) a burst stimulus consisting of 4×10 events at 100 Hz every 20 s, and (iii) sustained low frequency stimulation (100 events at 1 Hz) to induce short term de-potentiation. Data are reported as the mean EPSP rate of rise (=EPSP slope) 30 min after the burst stimulus protocol as a percentage of control values before the induction of LTP.

The stimulus-response relationship was normal in tissue from APP-null mice compared with the wild-type mice indicating that there were no gross changes in the efficiency of baseline excitatory synaptic transmission (FIG. 6A). The peak EPSP slope was not significantly different between APP-null (0.84±0.17 mV/ms) and wild-type mice (0.97±0.23 mV/ms). However, the ability of high frequency stimuli to induce LTP was impaired. This was a most pronounced statistically significant effect with the burst stimulus protocol, following which EPSPs were only potentiated by 197±22% compared to 271±27% in tissue from an isogenic wild-type mouse (C57×J129), or 296±25% in the control C57 mouse strain (t=30 min after stimulus, FIG. 6B). This was associated with a reduction in the EPSP slope immediately after the burst stimulus (2 min) implying that these effects may be in part due to a decrease in efficiency of LTP induction rather than its maintenance (FIG. 6C). Immunohistochemical staining (see below) of sections of the post-fixed contralateral hippocampus with the GFAP antibody showed reactive gliosis in hippocampi from the APP-null mice. Furthermore, the deficit in LTP was correlated with the extent of gliosis in the stratum radiatum of animals used for electrophysiological experiments (after Ln transformation $r^2=0.79$, $P<0.02$; FIG. 6D). Consequently, the deletion of the APP gene in mice results in impaired neuronal function within the hippocampus suggesting that the APP gene product is either required for normal synaptic development or may directly modulate cell function.

EXAMPLE 12

Immunohistochemistry

To determine whether any effects on LTP in the APP-null mice were associated with reactive gliosis and a change in synaptic markers within the hippocampus, the contralateral hippocampus from each animal was removed, post-fixed in 10% formalin and sections processed for immunohistochemistry so that the levels of GFAP immunoreactivity could be assayed in each animal. The analysis of the correlation between LTP deficits and levels of gliosis was also determined using a blind protocol.

For more sensitive and detailed immunohistochemistry, mice were deeply anaesthetised and transcardiacally perfused with saline followed by 10% formalin in 0.1M phosphate buffered saline (PBS). Brains were removed, post-fixed in 10% formalin in PBS for 24 h, sliced into coronal blocks which were then embedded in paraffin wax. Coronal sections (6 $\mu$m) were cut on a rotary microtome, deparaffinised, rinsed in PBS and treated with 0.03% $H_2O_2$ for 30 min (to block endogenous peroxidase activity). Background staining was blocked by incubating the sections in 3% normal horse serum for 1 h. Adjacent sections were incubated overnight at 4° C. with antibodies to either 1:1000 dilution of GFAP (rabbit polyclonal, DAKO), 1:100 dilution of MAP-2 (monoclonal, clone AP20, BOEHRINGER MANNHEIM), 1:1000 dilution of synaptophysin (monoclonal, clone SVP38, BOEHRINGER MANNHEIM) or 1:100 dilution of synapsin (BOEHRINGER MANNHEIM). Immunostaining was visualized using ABC elite system (VECTOR LABORATORIES, Peterborough, UK) followed by development in diaminobenzidine (DAB). Finally, sections were counterstained in Gill's haematoxylin, dehydrated and mounted for microscopical examination.

Earlier immunohistochemical studies (Zheng H., et al. (1995) Cell 81:525–531; which is incorporated by reference herein in it's entirety) with an antibody to glial fibrillary acidic protein (GFAP) showed marked reactive astrocytosis in many brain areas, but most predominantly in the cortex and hippocampus at 14 weeks of age (n=4/6). Since reactive astrocytosis is a sensitive marker for cell injury, these results may indicate that there is an early impairment in neuronal function in these mice as a result of the APP deletion. However, at this age no marked changes were seen in the staining patterns for synaptic markers, although presynaptic and dendritic changes (e.g. spine density) may be altered, but are undetectable by routine immunohistochemical analysis.

To complement the LTP data, six APP-null mice (eight to ten months old) were perfusion fixed and processed for immunohistochemistry with antibodies to GFAP, synaptophysin, synapsin and MAP-2. In all these brains the immunohistochemical analysis revealed no detectable differences in the levels of presynaptic markers, synapsin and synaptotrophysin and MAP-2, the dendritic marker. However, the astrocytosis previously described at four months persisted in the cortex and hippocampus of all the animals.

Immunohistochemical analysis of perfusion fixed brains from a group of APP-null mice (n=6) that were showing weight loss and hypolocomotor activity revealed severe morphological abnormalities. In addition to the reactive astrocytosis as detected by the enhanced GFAP immunoreactivity (FIGS. 7A and B), there was a substantial decrease in the staining for the presynaptic markers, synaptophysin and synapsin and the dendritic marker, MAP-2 (FIG. 7) in all cortical areas, but most profoundly in the frontal (FIG. 7A) and the entorhinal cortices and in the hippocampus (FIG. 7B). In the cortex, the decrease in synapsin and synaptophysin immunostaining was evident in all cortical layers, (FIG. 7A, panels b and f; c and g) while in the hippocampus this loss was evident throughout all the hippocampal fields, but most profoundly in the polymorphic layer (hilus) of the dentate gyrus and CA3 region (FIG. 7B, panels b and f; c and g). There was a substantial decrease in MAP-2 immunoreactivity in both the cortex especially in layer 1 (FIG. 7A, panels d and h) and hippocampus (FIG. 7B, panels d and h) of APP-null mice.

In the cortex, the decrease in MAP-2 was evident in all cortical layers, as was the loss of the long apical dendrites originating from the large pyramidal neurons in layer V which give rise to long axons that leave the cortex to innervate the basal ganglia, the brain stem and spinal cord. A significant loss of MAP-2 immunoreactivity in the hippocampus of APP-null mice was seen in the stratum radiatum, stratum lacunosum moleculare and in the molecular layer and in the hilus of the dentate gyrus and CA3 region. The loss of MAP-2 staining here may reflect a loss of CA3 pyramidal cell dendrites which receive inputs from the dentate granule cell axons (mossy fibres). Overall, the branching of dendrites of both cortical and hippocampal neurons of the APP-null mice was much less extensive than that seen in the wild-type mice. The loss of MAP-2 immunoreactive dendrites in the hippocampus resulted in an accumulation of MAP-2 in cell bodies which was clearly evident in the CA1 pyramidal cells and the dentate granule cells (FIG. 7B, panel h). Despite these presynaptic and dendritic changes in the cortex and hippocampus, detailed stereological analysis on these mice did not show any loss of cells in the cortex or hippocampus.

What is claimed is:

1. A transgenic mouse whose genome comprises a disruption of the gene encoding amyloid precursor protein (APP), wherein functional APP is not produced and the mouse exhibits a phenotype selected from impaired long-term potentiation, a decrease in presynaptic markers, a decrease in dendritic marker MAP-2 in the cortex, an increase of dendritic marker MAP-2 in CA1 pyramidal cells in the hippocampus or weight loss as compared to a wild-type mice.

2. The mouse of claim 1, wherein the mouse is fertile and transmits the disrupted gene to its offspring, where in the offspring exhibit a phenotype selected from impaired long-term potentiation, a decrease in presynaptic markers, a decrease in dendritic marker MAP-2 in the cortex, an increase of the dendritic marker MAP-2 in CA1 pyramidal cells in the hippocampus or weight loss as compared to wild-type mice.

3. The mouse of claim 1, wherein the mouse is produced by the introduction of a mouse embryonic stem cell into a mouse blastocyst, wherein the genome of the embryonic stem cell comprises a disruption of the gene encoding APP, and wherein functional APP is not produced by the embryonic stem cell.

4. The mouse of claim 3, wherein the introduction is by microinjection.

5. The mouse of claim 1, wherein the phenotype is impaired long-term potentiation.

6. The mouse of claim 1, wherein the phenotype is a decrease in presynaptic markers in the hippocampus.

7. The mouse of claim 1, wherein the phenotype is a decrease in dendritic marker MAP-2 in the cortex.

8. The mouse of claim 1, wherein the phenotype is an increase in dendritic marker MAP-2 in CA-1 pyramidal cells in the hippocampus.

9. A cell line derived from the mouse of claim 1, wherein the genome of the cell comprises a disruption of the gene encoding APP, and wherein functional APP is not produced by the cell.

10. A method of producing a mouse whose genome comprises a disruption of the gene encoding amyloid precursor protein (APP), the method comprising:
   (a) providing a gene encoding mouse APP, wherein the gene comprise a disruption such that function APP is not expressed from said gene;
   (b) introducing the disrupted gene into mouse embryonic stem cells;
   (c) selecting those embryonic stem cells that comprise the disrupted gene encoding APP;
   (d) introducing an embryonic stem cells of step (c) into a mouse blastocyst;
   (e) transferring the blastocyst of step (d) to pseudopregnant mouse, and
   (f) allowing the transferred blastocyst to develop into a mouse chimeric for the disruption.

11. The method of claim 10, wherein the introduction is by microinjection.

12. The method of claim 11, further comprising:
   (g) breeding the chimeric mouse to a wild-type mouse to obtain mice heterozygous for the disruption; and
   (h) breeding the heterozygous mice to generate mice homozygous for the disruption.

* * * * *